United States Patent
Ceballos et al.

(10) Patent No.: US 12,419,821 B2
(45) Date of Patent: Sep. 23, 2025

(54) ANTI-DANDRUFF CLEANSING COMPOSITION

(71) Applicant: L'OREAL, Paris (FR)

(72) Inventors: Ma Angellica Mangaban Ceballos, Hackensack, NJ (US); Allison Chin, Hobocken, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/993,875

(22) Filed: May 31, 2018

(65) Prior Publication Data

US 2019/0365619 A1    Dec. 5, 2019

(51) Int. Cl.
| | |
|---|---|
| *A61K 8/368* | (2006.01) |
| *A61K 8/41* | (2006.01) |
| *A61K 8/42* | (2006.01) |
| *A61K 8/46* | (2006.01) |
| *A61K 8/60* | (2006.01) |
| *A61Q 5/00* | (2006.01) |
| *A61Q 5/02* | (2006.01) |
| *A61Q 5/12* | (2006.01) |

(52) U.S. Cl.
CPC .............. *A61K 8/368* (2013.01); *A61K 8/416* (2013.01); *A61K 8/42* (2013.01); *A61K 8/466* (2013.01); *A61K 8/604* (2013.01); *A61Q 5/006* (2013.01); *A61Q 5/02* (2013.01); *A61Q 5/12* (2013.01); *A61K 2800/34* (2013.01); *A61K 2800/48* (2013.01); *A61K 2800/5426* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 5,137,715 | A * | 8/1992 | Hoshowski | A61K 8/463 424/70.17 |
| 6,333,027 | B1 * | 12/2001 | Hopkins | A61P 17/08 424/70.21 |
| 8,574,561 | B1 * | 11/2013 | Patel | A61K 8/27 424/401 |
| 9,006,162 | B1 | 4/2015 | Rizk | |
| 9,393,447 | B2 | 7/2016 | Zasloff | |
| 9,504,636 | B2 | 11/2016 | Klug et al. | |
| 9,539,185 | B2 | 1/2017 | Sato et al. | |
| 2003/0103927 | A1 * | 6/2003 | Maubru | A61K 8/8152 424/70.12 |
| 2004/0213754 | A1 * | 10/2004 | Cole | A61K 8/41 424/70.27 |
| 2005/0143267 | A1 * | 6/2005 | Piterski | C11D 3/38 510/124 |
| 2012/0213725 | A1 * | 8/2012 | Galleguillos | A61K 8/463 424/70.16 |
| 2013/0284198 | A1 * | 10/2013 | Rizk | A61K 8/731 132/202 |
| 2015/0125415 | A1 | 5/2015 | Klug et al. | |
| 2015/0126616 | A1 | 5/2015 | Klug et al. | |
| 2015/0133560 | A1 | 5/2015 | Klug et al. | |
| 2015/0140048 | A1 | 5/2015 | Klug et al. | |
| 2015/0141508 | A1 | 5/2015 | Klug et al. | |
| 2015/0164756 | A1 | 6/2015 | Klug et al. | |
| 2016/0074310 | A1 | 3/2016 | Klug et al. | |
| 2016/0136072 | A1 | 5/2016 | Klug et al. | |
| 2016/0143828 | A1 | 5/2016 | Klug et al. | |
| 2016/0272666 | A1 | 9/2016 | Klug et al. | |
| 2016/0361243 | A1 | 12/2016 | Klug et al. | |
| 2017/0000710 | A1 | 1/2017 | Klug et al. | |
| 2017/0002297 | A1 | 1/2017 | Klug et al. | |
| 2019/0105247 | A1 * | 4/2019 | Song | A61K 8/89 |

FOREIGN PATENT DOCUMENTS

| | | |
|---|---|---|
| DE | 20201710105 U1 | 10/2017 |
| WO | 2016062619 A1 | 4/2016 |
| WO | 2017216162 A1 | 12/2017 |
| WO | 2018002557 A1 | 1/2018 |

OTHER PUBLICATIONS

Baird "What are pearlizing agents in Shampoos".*
Annamarine Skin Care "Ingredient watch List: Glycol Distearate, the Fake Pearlescent Thickener".*
Curlynikki "Ingredients 101-Cationinc Surfactants" Apr. 5, 2012.*
Schefer "Conditioning Agents for Hair Formulations" Oct. 30, 2008.*
"Discover Value. Discover GlucoTain—A New Sensory Dimension," CLARIANT, 2015, pp. 1-27 http://www.in-cosmetics.com/RXUK/RXUK_InCosmetics/2015-Website/Documents/incos15,IS,T1,D2,GlucoTain%C2%AE%20surfactants%20A%20new%20mild%20and%20sustainable%20sensory%20dimension,Dr.%20Michael%20Waidelich.pdf?v=635658360710321750.
Mintel Database results, 2010, pp. 1-13 http://www.gnpd.com.
Mintel Database, "Concentrated Shower Gel"—2017, pp. 1-3 http://www.gnpd.com.

* cited by examiner

*Primary Examiner* — Danah Al-Awadi
(74) *Attorney, Agent, or Firm* — POLSINELLI PC

(57) ABSTRACT

The present disclosure relates to an anti-dandruff cleansing composition comprising:
(a) salicylic acid;
(b) a surfactant system comprising: (i) one or more non-sulfate anionic surfactants; (ii) one or more amphoteric surfactants; (iii) at least 10 wt. % of a plurality of nonionic surfactants comprising: (iii-a) one or more alkyl polyglucosides; and (iii-b) one or more amide surfactants; and
(c) water;
wherein all weight percentages are based on the total weight of the cleansing composition. The anti-dandruff cleansing compositions effectively treat dandruff and provide good cleansing and other desirable performance properties.
Therefore, the compositions are particularly useful in methods for treating dandruff, for cleansing hair, and for providing a variety of other cosmetic benefits to the hair.

13 Claims, No Drawings

ANTI-DANDRUFF CLEANSING COMPOSITION

FIELD OF THE DISCLOSURE

The present disclosure relates anti-dandruff cleansing compositions that effectively treat dandruff and provide good cleansing and other desirable performance properties.

BACKGROUND

The appearance of dandruff is troublesome both in terms of personal appearance and discomfort (itching, rash, etc.). Therefore, many individuals suffering from dandruff seek an effective and definitive treatment method. Dandruff is caused by excessive and visible desquamation of the scalp resulting from excessively rapid multiplication of the epidermal cells and their abnormal maturation. This can result from physical or chemical microtraumas caused by, for example, overly aggressive cleansings, extreme weather conditions, nerves, diet, fatigue, and pollution. Nonetheless, dandruff is most often the result of a scalp microflora disorder, and more particularly excessive colonization of yeast belonging to the *Malassezia* genus of yeasts (previously known as *Pytirosporum ovale*) which is naturally found on the scalp. Anti-fungal agents are commonly used to control dandruff by eliminating or reducing the multiplication of resident yeast on the scalp. Common anti-fungal agents include zinc pyrithione, piroctone olamine, and selenium disulfide, which can be included in an anti-dandruff shampoo.

Consumers find treating dandruff with a shampoo to be convenient because such treatment fit into the consumers' regular routine. Anti-dandruff shampoos provide cleansing benefits to the hair while simultaneously treating dandruff. In addition to anti-dandruff agents, anti-dandruff shampoos include cleansing surfactants. Anionic surfactants are often included because they provide foaming to the shampoo in addition to good cleansing properties. Nonionic surfactants may also be included to provide cleansing, solubilizing, and dispersing properties but are usually less irritating than anionic surfactants. Nonionic surfactants, however, often possess less foaming ability and do not provide any enhancement to viscosity (e.g., often times the composition is thinner and runnier with increased amounts of nonionic surfactants). In some cases, higher viscosity is desired for the product's handling or ease of application.

Anti-dandruff shampoos need to be effective for the treatment of dandruff and need to provide good cleansing properties to the hair without damaging the hair or causing excessive dryness to the hair. One drawback of some anti-dandruff agents and certain surfactants (e.g., sulfate-based surfactants) is their propensity to remove natural oils from the hair leaving the hair dry and brittle. It is challenging for consumers to find shampoos that cleanse well but do not deteriorate the hairs' natural shine, softness, and strength, especially anti-dandruff shampoos. Consumers also seek anti-dandruff shampoos that are aesthetically pleasing, stable, and easy to use, i.e., the shampoo should rinse away from the hair with ease. Unfortunately, the inclusion of an ingredient that provides or enhances one desired property often destabilizes or deteriorates another desired property. It is therefore difficult to achieve a perfect balance of desirable aesthetic properties, anti-dandruff efficacy, and cleansing; and is particularly difficult to obtain a perfect balance of desired performance properties while also ensuring that the product is stable.

SUMMARY OF THE DISCLOSURE

The instant disclosure relates to anti-dandruff cleansing compositions that effectively treat dandruff, cleanse the hair, and possess additional desirable qualities such as good foaming, lather, distribution, detangling, shine, smoothness, and discipline to hair. The anti-dandruff compositions include an anti-dandruff agent (salicylic acid). Salicylic acid has keratolytic and anti-inflammatory properties, and causes cells of the epidermis to shed more easily, helping to remove dry and flaky skin. Therefore, it is particularly useful for combating dandruff caused by scalp psoriasis and seborrheic dermatitis.

The anti-dandruff cleansing compositions of the instant disclosure include a unique surfactant system, which includes a combination of non-sulfate anionic surfactants, amphoteric surfactants, and nonionic surfactants. The total amount of nonionic surfactants is typically at least 10 wt. %, based on the total weight of the anti-dandruff cleansing composition.

More specifically, the anti-dandruff cleansing compositions include:
(a) about 1 to about 5 wt. % of salicylic acid;
(b) about 15 to about 45 wt. % of a surfactant system comprising:
 (i) about 1 to about 15 wt. % of one or more non-sulfate anionic surfactants;
 (ii) about 1 to about 15 wt. % of one or more amphoteric surfactants; and
 (iii) at least 10 wt. % of a plurality of nonionic surfactants comprising:
  (iii-a) about 1 to about 15 wt. % of one or more alkyl polyglucosides; and
  (iii-b) about 1 to about 15 wt. % of one or more amide surfactants; and
(c) water;
wherein all weight percentages are based on the total weight of the cleansing composition.

Non-limiting examples of non-sulfate anionic surfactants include alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, and a mixture thereof. In some cases, acyl isethionates are particularly useful.

Amphoteric surfactants include, for example, betaines, alkyl sultaines, alkyl amphoacetates, amphopropionates, salts thereof, and a mixture thereof. In some cases, betaines are particularly useful.

The plurality of nonionic surfactants in the anti-dandruff cleansing composition includes at least one alkyl polyglucoside, at least one amide surfactant, and optionally, one or more additional nonionic surfactants. Non-limiting examples of alkyl polyglucosides include lauryl glucoside, octyl glucoside, decyl glucoside, coco glucoside, caprylyl/caproyl glucoside, and lauryl/myristoyl glucoside.

Useful amide surfactants include fatty acid alkanolamides such as acyl glucamides, fatty acid alkanolamides that are not acyl glucamides, and a mixture thereof. Non-limiting examples of acyl glucamides include lauroyl/myristoyl methyl glucamide, capryloyl/caproyl methyl glucamide, lauroyl methyl glucamide, myristoyl methyl glucamide, capryloyl methyl glucamide, caproyl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide. Non-limiting examples of fatty acid alkanolamides that are not acyl glucamides include cocamide MEA (coco monoethanolamide) and cocamide MIPA (coco monoisopropanolamide), cocamide DEA (coco diethanolamide), cocamide DIPA (coco diisopropanolamine), lauramide MEA (lauryl monoethanolamide), and lauramide DEA (lauryl diethanolamide). In some cases, it is preferable to include at least two fatty acid alkanolamides. For example, it can be preferable to include one or more acyl glucamides and one or more fatty acid alkanolamides that are not acyl glucamides.

The plurality of nonionic surfactants is typically a major component of the surfactants system (and therefore a major component of the anti-dandruff cleansing compositions). For example, the total amount of all nonionic surfactants in the anti-dandruff cleansing compositions may be higher than the total amount of all anionic surfactants in the anti-dandruff cleansing compositions. Also, the total amount of all nonionic surfactants in the anti-dandruff cleansing compositions may be higher than the total amount of all amphoteric surfactants in the anti-dandruff composition. In fact, in some cases, the total amount of nonionic surfactants can be higher than the combined total of all anionic surfactants and all amphoteric surfactants in the anti-dandruff cleansing composition (the total amount of nonionic surfactants may be higher than the total amount of all other surfactants in the anti-dandruff cleansing combination combined).

The anti-dandruff cleansing compositions may also include one or more conditioning agents, water-soluble solvents, thickening agents, emollients, pH adjusters, salts, preservatives, etc. Non-limiting examples of conditioning agents include cationic polymers, non-silicone fatty compounds, silicones, cationic proteins, cationic protein hydrolysates, oils, ester oils, and alkylamines. Non-limiting examples of water-soluble solvents include, for example, organic solvents selected from glycerin, alcohols (for example, $C_{1-12}$, $C_{1-10}$, $C_{1-8}$, or $C_{1-4}$ alcohols), polyols (polyhydric alcohols), glycols, and a mixture thereof. Non-limiting examples of thickening agents include carboxylic acid polymers, crosslinked polyacrylate polymers, polyacrylamide polymers, polysaccharides, and gums.

The anti-dandruff cleansing compositions do not require silicones, film-forming polymers, and sulfate-based surfactants. Thus, any one or more (or all) of these may optionally be excluded from the cleansing compositions. In other words, the compositions may be free or essentially free of silicones and/or film-forming polymers and/or sulfate-based surfactants. Nonetheless, in some instances, one or more silicones and/or one or more film-forming polymers and/or one or more sulfate-based surfactants may optionally be included in the cleansing compositions.

The anti-dandruff cleansing compositions of the instant disclosure are particularly useful for treating dandruff and for cleansing and conditioning hair. The compositions exhibit good cleansing ability, lather, foaming and foam stability, and conditioning properties. Additionally, the cleansing compositions provide a variety of desirable styling benefits to the hair, for example, smoothness, detangling, and shine. Accordingly, the cleansing compositions may be used in methods for treating dandruff, methods for cleansing hair, methods for conditioning hair, and methods for imparting smoothness, detangling, and/or shine to hair.

DETAILED DESCRIPTION OF THE DISCLOSURE

The anti-dandruff cleansing compositions of the instant disclosure typically include:
(a) about 1 to about 5 wt. % of salicylic acid;
(b) about 15 to about 45 wt. % of a surfactant system comprising:
  (i) about 1 to about 15 wt. % of one or more non-sulfate anionic surfactants;
  (ii) about 1 to about 15 wt. % of one or more amphoteric surfactants; and
  (iii) at least 10 wt. % of a plurality of nonionic surfactants comprising:
    (iii-a) about 1 to about 15 wt. % of one or more alkyl polyglucosides; and
    (iii-b) about 1 to about 15 wt. % of one or more amide surfactants; and
(c) water;
  wherein all weight percentages are based on the total weight of the cleansing composition.

The anti-dandruff cleansing compositions treat dandruff, cleanse the hair, and even impart desirable conditioning properties to the hair, such as smoothness, detangling, and shine. Sulfate-based surfactants are often used in cleansing compositions because they are particularly strong cleansing agents. Nonetheless, they have a tendency to remove natural oils from the hair leaving the hair dry and brittle. The anti-dandruff cleansing compositions of the instant case provide strong cleansing action to the hair without the need for sulfate-based surfactants. Sulfate based surfactant may optionally be included in the anti-dandruff cleansing compositions but they are certainly not required, and are preferably excluded from the compositions.

Silicones are also commonly used in traditional cleansing compositions because they provide smoothness and conditioning to the hair. Silicones may optionally be included in the anti-dandruff cleansing compositions but are certainly not required and may be excluded. Silicones are not required because the anti-dandruff cleansing compositions of the instant case provide smoothness and conditioning without them.

The anti-dandruff cleansing compositions of the instant case also provide desirable styling properties to the hair without requiring use of film forming polymers. Film forming polymers are commonly used to provide styling benefits such as styling hold and shaping memory. Film forming polymers (including anionic, amphoteric, and nonionic film-forming polymers) may optionally be included in the instant cleansing compositions but are certainly not required and may be excluded, as the anti-dandruff cleansing compositions provide styling benefits without them.

Salicylic acid is a lipophilic monohydroxybenzoic acid, a type of phenolic acid, with the formula $C_7H_6O_3$. It functions as keratinolytic agent and assists in removing scaly hyperkeratotic skin. Although it is effective in treating dandruff, it tends to be difficult to formulate into stable cosmetic compositions, especially at therapeutically effective amounts. Without wishing to be bound by any particular theory, it is believed that the unique surfactant system, which includes a high amount of nonionic surfactants, contributes to the stability and effectiveness of the instant anti-dandruff cleansing compositions.

The surfactant system results from a combination of different surfactants, including anionic, amphoteric (zwitterionic), and nonionic surfactants. Anionic surfactants carry a negative charge on the polar head group. These surfactants are typically used for their detergency properties. They are highly effective at removing dirt and oil from the hair and scalp. Many amphoteric surfactants display pH-dependent charge behavior, having one charge at a lower pH and the opposite charge at a higher pH. These types of surfactants tend to be mild both to skin and hair. They can also provide foam-boosting properties in combination with anionic surfactants, which enhances lather. Nonionic surfactants are those that have no (or very little) residual electric charge. These surfactants can perform a variety of functions, such as emulsion stabilization, mild detergency and viscosity modification. Amphoteric (zwitterionic) surfactants are dual-charged (have both a positive and negative charge on the molecule). The combination of surfactants in the surfactant system of the instant disclosure, in high concentrations, provides the cleansing compositions with cleansing power, stabilizing properties, viscosity enhancement, and foaming.

The surfactant system of the instant disclosure includes: (i) one or more non-sulfate anionic surfactants; (ii) one or more amphoteric surfactants; and (iii) a plurality of nonionic surfactants. The plurality of nonionic surfactants includes, one or more alkyl polyglucosides, one or more amide surfactants, and optionally, one or more additional nonionic surfactants. The term "plurality," as used in the instant disclosure, means "more than one" or "two or more."

The plurality of nonionic surfactants is typically a major component of the surfactants system (and therefore a major component of the anti-dandruff cleansing compositions). For example, the total amount of all nonionic surfactants in the anti-dandruff cleansing compositions may be higher than the total amount of all anionic surfactants in the anti-dandruff cleansing compositions. Also, the total amount of all nonionic surfactants in the anti-dandruff cleansing compositions may be higher than the total amount of all amphoteric surfactants in the anti-dandruff composition. In fact, in some cases, the total amount of nonionic surfactants can be higher than the combined total of all anionic surfactants and all amphoteric surfactants in the anti-dandruff cleansing composition (the total amount of nonionic surfactants may be higher than the total amount of all other surfactants in the anti-dandruff cleansing combination combined). Without wishing to be bound by any particularly theory, it is believed that the unique combination of surfactants in the surfactant system, and the high amounts of nonionic surfactants in the surfactant system, contribute to the stability of the anti-dandruff cleansing compositions, which effectively incorporate salicylic acid at therapeutically effective levels.

Surfactant System

The total amount of surfactants in the anti-dandruff cleansing compositions is typically from about 15 to about 45 wt. %, based on the total weight of the anti-dandruff cleansing composition. In some instances, the total amount of surfactants ranges from about 15 to about 40 wt. %, about 15 to about 35 wt. %, about 15 to about 30 wt. %, about 20 to about 40 wt. %, about 20 to about 35 wt. %, about 25 to about 35 wt. %, based on the total weight of the anti-dandruff cleansing composition.

Useful but non-limiting examples of surfactants that may be used are provided below.

(i) Non-Sulfate Anionic Surfactants

The total amount of non-sulfate anionic surfactants in the anti-dandruff cleansing compositions can vary but typically ranges from about 1 to about 30 wt. %, based on the total weight of the anti-dandruff cleansing composition. In some cases, the total amount of non-sulfate anionic surfactants is from about 1 to about 20 wt. %, about 1 to about 15 wt. %, about 1 to about 10 wt. %, about 2 to about 30 wt. %, about 2 to about 20 wt. %, about 2 to about 15 wt. %, about 2 to about 10 wt. %, or about 3 to about 8 wt. %, based on the total weight of the anti-dandruff cleansing composition.

Useful non-sulfate anionic surfactants include, but are not limited to, alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, and a mixture thereof. In some cases, however, acyl isethionates are preferred and therefore the one or more non-sulfate anionic surfactants include at least one acyl isethionate. It is also preferable, in some instances, to include two or more acyl isethionates in the anti-dandruff cleansing compositions. Thus, the anti-dandruff cleansing compositions may include one or more non-sulfate anionic surfactants wherein at least one (and preferably two or more) of the anionic surfactants are selected from acyl isethionates.

Non-limiting examples of useful non-sulfate anionic surfactants are provided below.

(i-a) Acyl Isethionates

Non-limiting examples of useful acyl isethionates include those of formula (I) and (II):

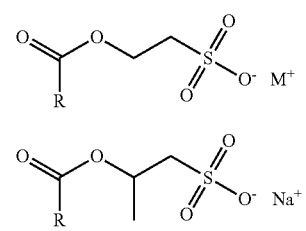

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Sodium is shown as the cation in formula (VI) but the cation for both formula (I) and formula (II) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate. In some embodiments, a combination of sodium isethionate and sodium cocoyl isethionate are preferable.

The total amount of acyl isethionate(s) in the cleansing composition, if present, may vary but is typically from about 0.1 to about 30 wt. %, based on the total weight of the anti-dandruff cleansing composition. In some cases, the total amount of acyl isethionate(s) is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

(i-b) Alkyl Sulfonates

Useful alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (III) is particularly useful.

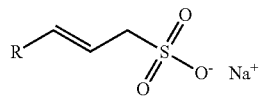
(III)

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and mixtures thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium C14-16 olefin sulfonate.

The total amount of alkyl sulfonate(s) in the cleansing compositions, if present, may range from about 0.1 to about 30 wt. %, based on the total weight of the anti-dandruff cleansing composition. In some cases, the total amount of alkyl sulfonate(s) is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

(i-c) Alkyl Sulfosuccinates

Non-limiting examples of useful sulfosuccinates include those of formula (IV):

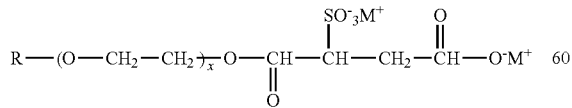
(IV)

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamide MIPA sulfosuccinate, disodium oleamide MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof. In some instances, disodium laureth sulfosuccinate is particularly preferred.

The total amount of alkyl sulfosuccinate(s) in the cleansing compositions, if present, may range from about 0.1 to about 30 wt. %, based on the total weight of the anti-dandruff cleansing composition. In some cases, the total amount of alkyl sulfosuccinate(s) is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

(i-d) Alkyl Sulfoacetates

Non-limiting examples of alkyl sulfoacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

The total amount of alkyl sulfoacetate(s) in the cleansing compositions, if present, may range from about 0.1 to about 30 wt. %, based on the total weight of the anti-dandruff cleansing composition. In some cases, the total amount of alkyl sulfoacetate(s) is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

(i-e) Alkoxylated Monoacids

Non-limiting examples of alkoxylated monoacids include compounds corresponding to formula (VII):

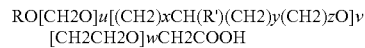

wherein:
R is a hydrocarbon radical containing from about 6 to about 40 carbon atoms;
u, v and w, independently of one another, represent numbers of from 0 to 60;
x, y and z, independently of one another, represent numbers of from 0 to 13;
R' represents hydrogen, alkyl, and
the sum of x+y+z>0;
Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trideceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof. In some cases, preferred ethoxylated acids include Oleth-10 Carboxylic Acid, Laureth-5 Carboxylic Acid, Laureth-11 Carboxylic Acid, and a mixture thereof.

The total amount of alkoxylated monoacid(s) in the cleansing compositions, if present, may range from about 0.1 to about 30 wt. %, based on the total weight of the anti-dandruff cleansing composition. In some cases, the total amount of alkoxylated monoacid(s) is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

(i-f) Acyl Amino Acids

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of useful acyl amino acids include those of formula (VIII):

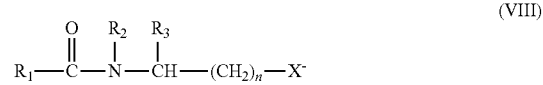

(VIII)

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$.

The total amount of acyl amino acids in the cleansing compositions, if present, may range from about 0.1 to about 30 wt. %, based on the total weight of the anti-dandruff cleansing composition. In some cases, the total amount of acyl amino acids is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

Acyl Taurates: Non-Limiting Examples of Acyl Taurates Include Those of Formula (IX):

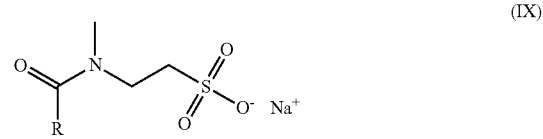

(IX)

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. Non-limiting examples of acyl taurate salts include sodium cocoyl taurate and sodium methyl cocoyl taurate.

The total amount of acyl taurates in the cleansing compositions, if present, may range from about 0.1 to about 30 wt. %, based on the total weight of the anti-dandruff cleansing composition. In some cases, the total amount of acyl taurates is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

Acyl Glycinates: Non-Limiting Examples of Useful Acyl Glycinates Include Those of Formula (X):

(X)

wherein R is an alkyl chain of 8 to 16 carbon atoms. Sodium is shown as the cation in the above formula (X) but the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

The total amount of acyl glycinates in the cleansing compositions, if present, may range from about 0.1 to about 30 wt. %, based on the total weight of the anti-dandruff cleansing composition. In some cases, the total amount of acyl glycinates is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

Acyl Glutamates: Non-Limiting Examples of Useful Acyl Glutamates Include Those of Formula (XI):

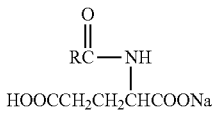
(XI)

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

The total amount of acyl glutamates in the cleansing compositions, if present, may range from about 0.1 to about 30 wt. %, based on the total weight of the anti-dandruff cleansing composition. In some cases, the total amount of acyl glutamates is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

Acyl Sarcosinates: Non-limiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate.

The total amount of acyl sarcosinates in the cleansing compositions, if present, may range from about 0.1 to about 30 wt. %, based on the total weight of the anti-dandruff cleansing composition. In some cases, the total amount of acyl sarcosinates is from about 0.1 to about 20 wt. %, about 0.1 to about 15 wt. %, about 0.1 to about 10 wt. %, about 0.1 to about 5 wt. %, about 1 to about 30 wt. %, about 1 to about 20 wt. %, about 1 to about 15 wt. %, about 1 to about 10 wt. %, about 1 to about 5 wt. %, about 2 to about 30 wt. %, about 2 to about 20 wt. %, about 2 to about 15 wt. %, about 2 to about 10 wt. %, or about 2 to about 5 wt. %, based on the total weight of the anti-dandruff cleansing composition.

(ii) Amphoteric Surfactants

The total amount of amphoteric surfactant(s) in the anti-dandruff cleansing compositions may vary but is typically from about 1 to about 30 wt. %, based on the total weight of the anti-dandruff cleansing composition. In some instance, the total amount of amphoteric surfactant(s) is about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 10 wt. %, or about 3 to about 10 wt. %, based on the total weight of the anti-dandruff cleansing composition.

Useful amphoteric surfactants include betaines, alkyl sultaines, alkyl amphoacetates, alkyl amphopropionates, and mixtures thereof. In some cases betaines are preferred and therefore the anti-dandruff compositions may include one or more amphoteric surfactants wherein at least one of the one or more amphoteric surfactants is a betaine. Non-limiting examples of useful amphoteric surfactants are provided below.

(ii-a) Betaines

Useful betaines include those of the following formulae (XIIIa-XIIId):

(XIIIa)

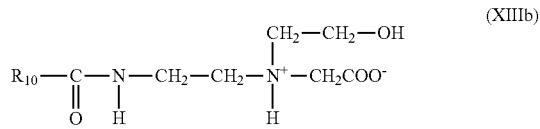
(XIIIb)

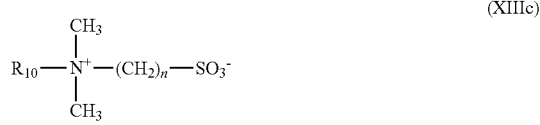
(XIIIc)

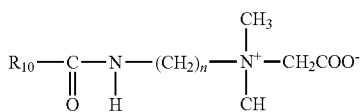

(XIIId)

wherein $R_{10}$ is an alkyl group having 8-18 carbon atoms; and n is an integer from 1 to 3.

Particularly useful betaines include, for example, coca betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof. Typically, at least one betaine compound is selected from coco betaine, cocamidopropyl betaine, behenyl betaine, capryl/capramidopropyl betaine, and lauryl betaine, and mixtures thereof. Particularly preferred betaines include coco betaine and cocamidopropyl betaine.

The total amount of betaines in the anti-dandruff cleansing compositions, if present, may vary but is typically from about 1 to about 30 wt. %, based on the total weight of the anti-dandruff cleansing composition. In some instance, the total amount of betaines is about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 10 wt. %, or about 3 to about 10 wt. %, based on the total weight of the anti-dandruff cleansing composition.

(ii-b) Alkyl Sultaines

Non-Limiting Examples of Alkyl Sultaines Include Hydroxyl Sultaines of Formula (XIV)

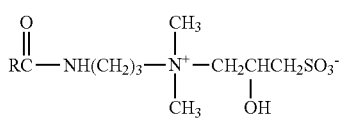

(XIV)

wherein R is an alkyl group having 8-18 carbon atoms. More specific examples include, but are not limited to cocamidopropyl hydroxysultaine, lauryl hydroxysultaine, and a mixture thereof.

The total amount of alkyl sultaines in the anti-dandruff cleansing compositions, if present, may vary but is typically from about 1 to about 30 wt. %, based on the total weight of the anti-dandruff cleansing composition. In some instance, the total amount of alkyl sultaines is about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 10 wt. %, or about 3 to about 10 wt. %, based on the total weight of the anti-dandruff cleansing composition.

(ii-c) Alkyl Amphoacetates and Alkyl Amphodiacetates

Useful alkyl amphoacetates and alkyl amphodiacetates include those of Formula (XV) and (XVI):

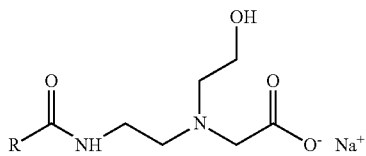

(XV)

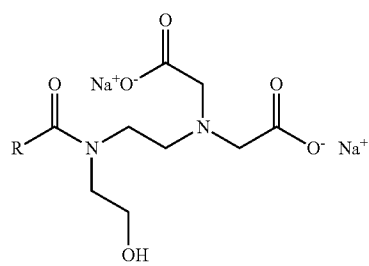

(XVI)

wherein R is an alkyl group having 8-18 carbon atoms. Sodium is shown as the cation in the above formulae above but the cation may be an alkali metal ion such as sodium or potassium, ammonium ions, or alkanolammonium ions such as monoethanolammonium or triethanolammonium ions. A more specific, but non-limiting example, is sodium lauroamphoacetate.

The total amount of alkyl amphoacetates and/or alkyl amphodiacetates in the anti-dandruff cleansing compositions, if present, may vary but is typically from about 1 to about 30 wt. %, based on the total weight of the anti-dandruff cleansing composition. In some instance, the total amount of alkyl amphoacetates and/or alkyl amphodiacetates is about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 10 wt. %, or about 3 to about 10 wt. %, based on the total weight of the anti-dandruff cleansing composition.

(ii-d) Alkyl Amphopropionates

Non-limiting examples of alkyl amphopropionates include cocoamphopropionate, cornamphopropionatecaprylamphopropionate, cornamphopropionate, caproamphopropionate, oleoamphopropionate, isostearoamphopropionate, stearoamphopropionate, lauroamphopropionate, salts thereof, and a mixture thereof.

The total amount of alkyl amphopropionates in the anti-dandruff cleansing compositions, if present, may vary but is typically from about 1 to about 30 wt. %, based on the total weight of the anti-dandruff cleansing composition. In some instance, the total amount of alkyl amphopropionates is about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 10 wt. %, or about 3 to about 10 wt. %, based on the total weight of the anti-dandruff cleansing composition.

(iii) Nonionic Surfactants

The anti-dandruff cleansing compositions include a plurality of nonionic surfactants. The term "plurality" means more than one," "two or more" or "at least two." The plurality of nonionic surfactants includes at least one alkyl polyglucoside and at least one amide surfactant. The total amount of nonionic surfactants in the anti-dandruff compositions is typically at least 10 wt. %, based on the total weight of the anti-dandruff compositions. While not wishing to be bound by any particular theory, it is believed that having at least 10 wt. % of nonionic surfactants helps to stabilize the anti-dandruff compositions. Thus, the total amount of nonionic surfactants may be from at least 10 to about 30 wt. %, based on the total weight of the anti-dandruff cleansing composition. In some cases, the total amount of the nonionic surfactants may be at least 10 to about 25 wt. %, at least 10 to about 20 wt. %, at least 10 to about 18 wt. %, at least 11 to about 30 wt. %, at least 11 to about 25 wt. %, at least 11 to about 20 wt. %, at least 11 to about 18 wt. %, based on the total weight of the anti-dandruff cleansing composition.

(iii-a) Alkyl Polyglucosides

The total amount of alkyl polyglucoside(s) in the anti-dandruff cleansing compositions may vary but is typically from about 1 to about 15 wt. %, based on the total weight of the anti-dandruff cleansing composition. In some instance, the total amount of alkyl polyglucoside(s) is about 1 to about 12 wt. %, is about 1 to about 10 wt. %, about 2 to about 15 wt. %, about 2 to about 12 wt. %, about 2 to about 10 wt. %, or about 3 to about 10 wt. %, based on the total weight of the anti-dandruff cleansing composition.

Non-limiting but useful alkyl polyglucosides include alkyl polyglucosides having the following formula (XII):

$$R^1-O-(R^2O)_n-Z(x) \quad (XII)$$

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Non-limiting examples of alkyl poly glucosides include lauryl glucoside, octyl glucoside, decyl glucoside, coca glucoside, sucrose laurate, caprylyl/capryl glucoside, and sodium lauryl glucose carboxylate, and mixtures thereof. Typically, the at least one alkyl poly glucoside compound is selected from the group consisting of lauryl glucoside, decyl glucoside, and coca glucoside. In some instances, lauryl and/or decyl glucoside are particularly preferred.

(iii-b) Amide Surfactants

The total amount of amide surfactants in the anti-dandruff cleansing compositions may vary but is typically from about 1 to about 20 wt. %, based on the total weight of the anti-dandruff cleansing composition. In some instance, the total amount of amide surfactants is about 1 to about 15 wt. %, about 1 to about 12 wt. %, about 1 to about 10 wt. %, about 2 to about 20 wt. %, about 2 to about 15 wt. %, about 2 to about 12 wt. %, about 2 to about 10 wt. %, or about 3 to about 20 wt. %, about 3 to about 15 wt. %, about 3 to about 12 wt. %, or about 3 to about 10 wt. %, based on the total weight of the anti-dandruff cleansing composition.

Non-limiting examples of amide surfactants include alkanolamides such as fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples thereof include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In an embodiment, the fatty acid alkanolamides include cocamide MIPA, cocamide DEA, cocamide MEA, cocamide DIPA, and mixtures thereof.

In an embodiment, the fatty acid alkanolamides is selected from cocamide MIPA commercially available under the tradename EMPILAN from Innospec Active Chemicals.

Additional non-limiting examples of fatty acid alkanolamides include oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

Fatty Acid Alkanolamides Include Those of the Following Structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);

$R_6$ is selected from —$CH_2OH$, —$CH_2CH_2OH$, —$CH_2CH_2CH_2OH$, —$CH_2(CHOH)_4CH_2OH$, -benzyl, and mixtures thereof;

$R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

In some instances, the one or more of the fatty acid alkanolamides are preferably acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide. The anti-dandruff cleansing compositions may therefore include a plurality of nonionic surfactants comprising: (a) one or more alky polyglucosides; and (b) one or more fatty acid alkanolamides, wherein at least one of the one or more fatty acid alkanolamides is an acyl glucoside, for example an acyl glucoside selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and a mixture thereof.

It can be particularly preferable to include one or more acyl glucamides together with one or more additional fatty acid alkanolamides that are not acyl glucosides. For examples, the plurality of nonionic surfactants may comprise: (a) one or more alky polyglucosides; and (b) two or more fatty acid alkanolamides, wherein at least one of the two or more fatty acid alkanolamides is an acyl glucoside (for example an acyl glucoside selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, or a mixture thereof) and at least one of the two or more fatty acid alkanolamides is not an acyl glucoside (for example, cocamide MIPA, cocamide DEA, cocamide MEA, cocamide DIPA, or a mixture thereof). A particularly preferred combination of fatty acid alkanolamides is lauroyl/myristoyl methyl glucamide and cocamide MIPA.

(iii-c) Additional Nonionic Surfactants

The anti-dandruff cleansing compositions may optionally include one or more additional nonionic surfactants, i.e., one or more nonionic surfactants in addition to the alkyl polyglucosides and amide surfactants discussed above.

The total amount of additional nonionic surfactant(s), if present, can vary but may be in an amount of from about 0.01 to about 25 wt. %, based on the total weight of the cleansing composition. In some instance, the total amount of miscellaneous nonionic surfactant(s) in the cleansing composition is from about 0.01 to about 20 wt. %, from about 0.01 to about 15 wt. %, about 0.01 to about 10 wt. %, from about 0.01 to about 5 wt. %, from about 0.1 to about 25 wt. %, from about 0.1 to about 20 wt. %, from about 0.1 to about 15 wt. %, or from about 0.1 to about 10 wt. %, or about 0.1 to about 5 wt. %, based on the total weight of the cleansing composition.

The nonionic surfactant(s) can be, for example, selected from alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$) alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Such nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Conditioning Agents

The total amount of conditioning agent(s) in the anti-dandruff cleansing compositions can vary but is typically from about 0.1 to about 10 wt. %, based on the total weight of the cleansing composition. In some instances, the total amount of conditioning agent(s) in the cleansing compositions is from about 0.1 to about 8 wt. %, from about 0.1 to about 6 wt. %, or from about 0.1 to about 5 wt. %, based on the total weight of the anti-dandruff cleansing composition.

Non-limiting examples of conditioning agents include alkylamines, cationic polymers, non-silicone fatty compounds, silicones, cationic proteins, cationic protein hydrolysates, oils, ester oils, and a mixture thereof. In some instances, alkylamines are the preferred conditioning agents, in particular amidoamines. Accordingly, in some instances, the anti-dandruff compositions include one or conditioning agents, wherein at least one of the one or more conditioning agents is an alkylamine, in particular, an amidoamine. Various conditioning agents, including amidoamines are described in more detail below.

(b-i) Alkylamines

Non-limiting examples of alkylamines that can be used in the anti-dandruff cleansing compositions include dimethylamine derivatives, such as for example stearyl dimethyl amine, stearamidopropyl dimethylamine, brassicamidopropyl dimethylamine, and mixtures thereof. Other non-limiting examples of alkylamines that can be used include amidoamines. Amidoamines are a class of chemical compounds that are formed from fatty acids and diamines. Non-limiting examples of amidoamines include those of the following formula:

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. In some cases, R" is H or a methyl group.

Non-limiting examples of amidoamines include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallowamidopropyl dimethylamine, brassicamidopropyl dimethylamine, olivamidopropyl dimethylamine, palmitamidopropyl dimethylamine, stearamidoethyldiethylamine, and a mixture thereof. In some cases, brassicamidopropyl dimethylamine may be particularly useful.

In some cases, the anti-dandruff cleansing compositions include stearamidopropyl dimethylamine. In some cases, the anti-dandruff cleansing compositions include brassicamidopropyl dimethylamine. In some instances, the alkylamine may be selected from octylamine, decylamine, dodecylamine, stearylamine, stearyl dimethyl amine, and a mixture thereof.

Also useful are tertiary amidoamines having an alkyl group of from about 12 to about 22 carbons. Exemplary tertiary amido amines include: brassicamidopropyl dimethylamine, stearamidopropyldimethylamine, stearamidopropyldimethylamine, stearamidoethyldiethylamine, stearamido-ethyldimethylamine, palmitamidopropyldimethylamine, palmitamidopropyldiethylamine, palmitamidoethyldiethylamine, palmitamidoethyldimethylamine, behenamidopropyl-dimethylamine, behenamidopropyldiethylamine, behenamidoethyldimethylamine, behenamidoethyldimethylamine, arachidamidopropyldimethylamine, arachidamidopropyldimethylamine, arachidamidoethyidiethylamine, arachidamidoethyidimethylamine, diethylaminoethylstearamide.

These amines may be used in combination with acids such as 1-glutamic acid, lactic acid, hydrochloric acid, malic acid, succinic acid, acetic acid, fumaric acid, tartaric acid, citric acid, 1-glutamic hydrochloride, maleic acid, and mixtures thereof; more preferably 1-glutamic acid, lactic acid, and citric acid.

(b-ii) Cationic Conditioning Polymers

The cationic conditioning polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a mixture thereof.

The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus when the polymer is not a homopolymer it can contain spacer non-cationic monomer units.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallylammonium chloride homopolymer and copolymers of acrylamide and dimethyldiallylammonium chloride (referred to as Polyquaternium-6 and Polyquaternium-7).

Other cationic conditioning polymers that can be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200.

Other cationic conditioning polymers that can be used include cationic guar gum derivatives, such as guar hydroxypropyltrimonium chloride.

Polyquaterniums include Polyquaternium-1 (ethanol, 2,2', 2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylene oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethyl-methacrylate and butylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-aminopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

In some instances, the cleansing compositions of the instant disclosure include one or more cationic conditioning polymers selected from cationic cellulose derivatives, quaternized hydroxyethyl cellulose (e.g., polyquaternium-10), cationic starch derivatives, cationic guar gum derivatives, copolymers of acrylamide and dimethyldiallylammonium chloride (e.g., polyquaternium-7), polyquaterniums, and a mixture thereof. In one particularly preferred embodiment, the cationic conditioning polymer(s) are selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and a mixture thereof. In particular, a combination of two or more polyquaterniums can be particularly useful, for example, a combination of polyquaternium-7 and polyquaternium-10.

(b-iii) Non-Silicone Fatty Compounds

The term "non-silicone fatty compound" means a fatty compound that does not containing any silicon atoms (Si). Non-limiting examples of non-silicone fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arachidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyl-dodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting examples of polyglycerol esters of fatty acids include those of the following formula:

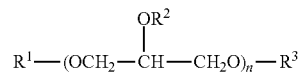

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in the International Cosmetic Ingredient Dictionary, Sixteenth Edition, 2016, which is incorporated by reference herein in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

In some instances, the non-silicone fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a mixture thereof.

In one embodiment, the personal care composition includes 10-30% of a combination of waxes. Mention may be made, among the waxes capable of being used as non-silicone fatty compounds, of animal waxes, such as beeswax; vegetable waxes, such as sunflower seed (*Helianthus annuus*), carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In some instance, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelargonate; and triesters, such as glyceryl trioctanoate. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, oxododecanal, or combinations of octyldodecanol, acetylated lanolin alcohol, cetyl acetate, isododecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

(b-iv) Silicones

The conditioning agent(s) of the cleansing compositions may optionally include one or more silicones. Nonetheless, as mentioned throughout the instant disclosure, in some instances the cleansing compositions are free or essentially free of silicones. In other words, one or more of the following silicones may be optionally included or optionally excluded from the cleansing compositions.

Silicones include, but are not limited to, polyorganosiloxanes, polyalkylsiloxanes, polyarylsiloxanes, polyalkylsiloxanes, polyestersiloxanes, and a mixture thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a mixture thereof.

In some instances, the cleansing compositions include (or exclude) one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, and mixtures thereof.

The cleansing compositions may include (or exclude) one or more silicone oils, for example one or more non-phenyl silicone oils and/or one or more phenyl silicone oils. The silicone oil is preferably apolar. An "apolar silicone oil" is intended to denote a silicon oil that does not comprise any ionic or ionisable group(s), and preferably does not comprise any oxyalkylenated($C_2$-$C_4$) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is preferably chosen from non-volatile dimethicone oils. In particular, these oils can be chosen from the following non-volatile oils:

polydimethylsiloxanes (PDMSs),

PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt, PDMSs comprising aliphatic groups, or functional groups such as hydroxyl, thiol and/or amine groups, [ polyalkylmethylsiloxanes substituted with functional groups such as hydroxyl, thiol and/or amine groups, polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular $C_2$-$C_{24}$ alkyl groups, and/or functional groups such as hydroxyl, thiol and/or amine groups.

The non-phenyl silicone oil may be chosen in particular from silicones of the following formula:

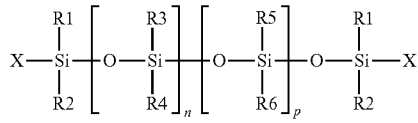

in which:
- $R_1$, $R_2$, $R_5$ and $R_6$ are, together or separately, an alkyl radical containing 1 to 6 carbon atoms,
- $R_3$ and $R_4$ are, together or separately, an alkyl radical containing from 1 to 6 carbon atoms, a vinyl radical, an amine radical or a hydroxyl radical,
- X is an alkyl radical containing from 1 to 6 carbon atoms, a hydroxyl radical or an amine radical,
- n and p are integers chosen so as to have a fluid compound, in particular of which the viscosity at 25° C. is between 9 centistokes (cSt) and 800,000 (cSt).

As non-volatile non-phenyl silicone oils which can be used according to the invention, mention may be made of those for which:
- the substituents $R_1$ to $R_6$ and X represent a methyl group, and p and n are such that the viscosity is 500,000 cSt, for example the product sold under the name SE30 by the company General Electric, the product sold under the name AK 500,000 by the company Wacker, the product sold under the name Mirasil DM 500,000 by the company Bluestar, and the product sold under the name Dow Corning 200 Fluid 500,000 cSt by the company Dow Corning,
- the substituents $R_1$ to $R_6$ and X represent a methyl group, and p and n are such that the viscosity is 60,000 cSt, for example the product sold under the name Dow Corning 200 Fluid 60,000 CS by the company Dow Corning, and the product sold under the name Wacker Belsil DM 60,000 by the company Wacker,
- the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning,
- the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

(b-v) Cationic Proteins and Cationic Protein Hydrolysates

Cationic proteins and cationic protein hydrolysates can be derived from animals, for example from collagen, milk, or keratin, from plants, for example from wheat, corn, rice, potatoes, soy, moringa, or almonds, from marine life forms, for example from fish collagen or algae, or from biotechnologically obtained protein hydrolysates. Those cationic protein hydrolysates may have a molecular weight from 100 to 25,000 dalton, from 250 to 5,000 dalton, or from 250 to 1000 dalton. Also to be understood as cationic protein hydrolysates are quaternized amino acids and mixtures thereof. Quaternization of the protein hydrolysates or of the amino acids is often carried out by means of quaternary ammonium salts such as, for example, N,N-dimethyl-N-(n-alkyl)-N-(2-hydroxy-3-chloro-n-propyl)ammonium halides. Typical examples that may be mentioned of cationic protein hydrolysates and derivatives according to the present invention are the products listed under the INCI names in the "International Cosmetic Ingredient Dictionary and Handbook," (seventh edition 1997, The Cosmetic, Toiletry, and Fragrance Association), which is incorporated herein by reference in its entirety. Non-limiting examples of Cationic protein hydrolysates include: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

Plant-based cationic proteins and cationic protein hydrolysates include but are not limited to those based on wheat, rice, corn, soy, almond, or moring, etc. Examples of cationic protein hydrolysates based on wheat include the commercial products GLUADIN WQ, GLUADIN WQT, and the HYDROTRITICUM series of the Croda company.

Water-Soluble Solvents

The cleansing compositions may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%.

The total amount of water-soluble solvents in the antidandruff cleansing compositions, if present, may vary but are typically in an amount of about 0.01 to about 20 wt. %, based on the total weight of the cleansing composition. In some instances, the total amount of water-soluble solvents may be from about 0.01 to about 15 wt. %, about 0.01 to about 10 wt. %, about 0.01 to about 5 wt. %, about 0.1 to about 20 wt. %, about 0.1 to about 15 wt. %, about 0.1 to about 10 wt. %, about 0.1 to about 5 wt. %, based on the total weight of the anti-dandruff cleansing composition.

Non-limiting examples of water-soluble solvents include, for example, organic solvents selected from glycerin, alcohols (for example, $C_{1-12}$, $C_{1-10}$, $C_{1-8}$, or $C_{1-4}$ alcohols), polyols (polyhydric alcohols), glycols, and a mixture thereof.

As examples of organic solvents, non-limiting mention can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2, 5-hexanediol, 5-hexene-1,2-diol, and 2-ethyl-1,3-hexanediol, and a mixture thereof.

Thickening Agents

The hair-treatment compositions may optionally contain one or more thickening agents (also referred to as thickeners or viscosity modifying agents). Many thickening agents are water-soluble, and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

The total amount of thickening agent(s) in the cleansing compositions, if present, may vary but are typically in an amount of from about 0.01 to about 10 wt. %, from based on the total weight of the cleansing composition. In some instances, the total amount of thickening agent in the cleansing composition is from about 0.01 to about 8 wt. %, from about 0.01 to about 6 wt. %, from about 0.01 to about 5 wt. %, from about 0.05 to about 10 wt. %, from about 0.05 to about 8 wt. %, from about 0.05 to about 6 wt. %, from about 0.05 to about 5 wt. %, from about 0.1 to about 10 wt. %, from about 0.1 to about 8 wt. %, from about 0.1 to about 6 wt. %, or from about 0.1 to about 5 wt. %, based on the total weight of the cleansing composition.

Non-limiting examples of thickening agents include xanthan gum, guar gum, biosaccharide gum, cellulose, acacia Seneca gum, *sclerotium* gum, agarose, pechtin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer.

In some instances, the thickening agent(s) are selected from carboxylic acid polymers (e.g., carbomer), crosslinked polyacrylate polymers, polyacrylamide polymers, polysaccharides, gums, and a mixture thereof. A more detailed description of various thickening agents is provided below.
(i) Carboxylic Acid Polymers These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

(ii) Crosslinked Polyacrylate Polymers

The compositions of the present disclosure can optionally contain crosslinked polyacrylate polymers useful as thickeners or gelling agents including both cationic and nonionic polymers.

(iii) Polyacrylamide Polymers

The compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

(iv) Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

(v) Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosaccharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, furcellaran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydialkyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Film-Forming Polymers

The cleansing compositions of the instant disclosure do not require film-forming polymers (including anionic, amphoteric, and nonionic film-forming polymers). However, one or more filming-forming polymers may optionally be included. Therefore, the cleansing compositions may optionally include or exclude (may be free or essentially free of) one or more film forming polymers. Non-limiting examples of film-forming polymers that may optionally be included or excluded from the cleansing compositions include vinyl polymers, polyesters, polyamides, polyureas, and a mixture thereof. The one or more film-forming polymers may be polyethyleneimine, polylysine, polyvinyl alcohols, poly(hydroxyethyl (meth)acrylate), hydroxyalkylcelluloses, polyacrylic acid, polyvinylimidazoles, polypropyleneimines, polyallylamines, chitosan, carboxyalkylcelluloses, aminoalkylcelluloses, maleic, fumaric and/or itaconic acid or anhydride polymers, polyamidoamines, and a mixture thereof.

The one or more film-forming polymers may be copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl(meth)acrylate and/or isobutyl (meth)acrylate/ $C_1$-$C_4$ alkyl(meth)acrylate copolymers; (meth)acrylic acid/ ethyl acrylate/methyl methacrylate terpolymers and tetrapolymers; methyl methacrylate/butyl or ethyl acrylate/ hydroxyethyl or 2-hydroxypropyl acrylate or methacrylate/ (meth)acrylic acid tetrapolymers; copolymers of acrylic acid and of $C_1$-$C_4$ alkyl methacrylate; terpolymers of vinylpyrrolidone, of acrylic acid and of $C_{1\text{-}20}$ alkyl methacrylate; amphoteric copolymers; vinyl esters of branched acids; vinyl esters of benzoic acid; copolymers of (meth)acrylic acid and of at least one olefinic monomer; copolymers of vinyl monoacid and/or of allylic monoacid; and a mixture thereof. In some cases, the one or more film-forming polymers include VP/dimethylaminoethylmethacrylate copolymer.

The cleansing compositions do not require silicones, film-forming polymers, and sulfate-based surfactants. Thus, any one or more (or all) of these may optionally be excluded from the cleansing compositions. In other words, the compositions may be free or essentially free of silicones and/or film-forming polymers and/or sulfate-based surfactants. Nonetheless, in some instances, one or more silicones and/or one or more film-forming polymers and/or one or more sulfate-based surfactants may optionally be included in the cleansing compositions.

In certain embodiments of the instant disclosure, the anti-dandruff cleansing compositions include:
 (a) about 1 to about 5 wt. %, preferably about 2 to about 4 wt. %, more preferably about 3 wt. % of salicylic acid;
 (b) about 15 to about 45 wt. %, preferably about 20 to about 40 wt. %, or more preferably about 25 to about 35 wt. % of a surfactant system comprising:
  (i) about 1 to about 15 wt. %, preferably about 2 to about 12, more preferably about 3 to about 10 wt. % of one or more non-sulfate anionic surfactants;
  (ii) about 1 to about 15 wt. %, preferably about 2 to about 12, more preferably, about 3 to about 10 wt. % of one or more amphoteric surfactants;
  (iii) at least 10 to about 30 wt. %, preferably at least 10 to about 25 wt. %, more preferably at least 10 to about 20 wt. % of a plurality of nonionic surfactants comprising:
   (iii-a) about 1 to about 15 wt. %, preferably about 2 to about 12, more preferably about 3 to about 10 wt. % of one or more alkyl polyglucosides; and
   (iii-b) about 1 to about 20 wt. %, preferably about 2 to about 15, more preferably about 3 to about 12 wt. % of one or more of one or more amide surfactants, preferably one or more fatty acid alkanolamides; and
 (c) 40 to about 90 wt. %, preferably about 50 to about 85 wt. %, more preferably about 60 to about 80 wt. % of water; and
 (d) optionally, about 0.01 to about 10 wt. %, preferably about 0.01 to about 5 wt. %, more preferably about 0.1 to about 5 wt. % of one or more conditioning agents;
 wherein all weight percentages are based on the total weight of the cleansing composition.

The surfactants of the surfactant system and the conditioning agent(s) in the embodiment above may be any of those described throughout the instant disclosure. Additionally, as noted above, the anti-dandruff cleansing compositions do not require silicones, film-forming polymers, and sulfate-based surfactants. Thus, any one or more (or all) of these may optionally be excluded from the anti-dandruff cleansing compositions. In other words, the compositions may be free or essentially free of silicones and/or film-forming polymers and/or sulfate-based surfactants. Nonetheless, in some instances, one or more silicones and/or one or more film-forming polymers and/or one or more sulfate-based surfactants may optionally be included in the cleansing compositions.

In yet further embodiments of the instant disclosure, the concentrated cleansing compositions include:
 (a) about 1 to about 5 wt. %, preferably about 2 to about 4 wt. %, more preferably about 3 wt. % of salicylic acid;
 (b) about 15 to about 45 wt. %, preferably about 20 to about 40 wt. %, or more preferably about 25 to about 35 wt. % of a surfactant system comprising:
  (i) about 1 to about 15 wt. %, preferably about 2 to about 12, more preferably about 3 to about 10 wt. % of one or more non-sulfate anionic surfactants selected from acyl isethionates;
  (ii) about 1 to about 15 wt. %, preferably about 2 to about 12, more preferably, about 3 to about 10 wt. % of one or more amphoteric surfactants selected from betaines;
  (iii) at least 10 to about 30 wt. %, preferably at least 10 to about 25 wt. %, more preferably at least 10 to about 20 wt. % of a plurality of nonionic surfactants comprising:
   (iii-a) about 1 to about 15 wt. %, preferably about 2 to about 12, more preferably about 3 to about 10 wt. % of one or more alkyl polyglucosides; and
   (iii-b) about 1 to about 20 wt. %, preferably about 2 to about 15, more preferably about 3 to about 12 wt. % of one or more of one or more fatty acid alkanolamides, wherein at least one of the fatty acid alkanolamides is an acyl glucamide; and
 (c) 40 to about 90 wt. %, preferably about 50 to about 85 wt. %, more preferably about 60 to about 80 wt. % of water; and
 (d) optionally, about 0.01 to about 10 wt. %, preferably about 0.01 to about 5 wt. %, more preferably about 0.1 to about 5 wt. % of one or more conditioning agents, wherein at least one of the one or more conditioning agents selected from amidoamines;
 wherein all weight percentages are based on the total weight of the cleansing composition.

The surfactants of the surfactant system and the conditioning agent (the amidoamines) in the embodiment above may be any of those described throughout the instant disclosure. Additionally, as noted above, the anti-dandruff cleansing compositions do not require silicones, film-forming polymers, and sulfate-based surfactants. Thus, any one or more (or all) of these may optionally be excluded from the cleansing compositions. In other words, the compositions may be free or essentially free of silicones and/or film-forming polymers and/or sulfate-based surfactants. Nonetheless, in some instances, one or more silicones and/or one or more film-forming polymers and/or one or more sulfate-based surfactants may optionally be included in the cleansing compositions.

In yet further embodiments of the instant disclosure, the concentrated cleansing compositions include:
 (a) about 1 to about 5 wt. %, preferably about 2 to about 4 wt. %, more preferably about 3 wt. % of salicylic acid;
 (b) about 15 to about 45 wt. %, preferably about 20 to about 40 wt. %, or more preferably about 25 to about 35 wt. % of a surfactant system comprising:
  (i) about 1 to about 15 wt. %, preferably about 2 to about 12, more preferably about 3 to about 10 wt. % of one or more acyl isethionates selected from sodium isethionate, sodium cocoyl isethionate, sodium lauroyl methyl isethionate, sodium cocoyl methyl isethionate, and a mixture thereof, preferably sodium isethionate, sodium cocoyl isethionate, or a mixture thereof;
  (ii) about 1 to about 15 wt. %, preferably about 2 to about 12, more preferably, about 3 to about 10 wt. % of one or more betaines selected from coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and a mixture thereof, preferably coco betaine, cocoamidopropyl betaine, or a mixture thereof;
   (iii) at least 10 to about 30 wt. %, preferably at least 10 to about 25 wt. %, more preferably at least 10 to about 20 wt. % of a plurality of nonionic surfactants comprising:
      (iii-a) about 1 to about 15 wt. %, preferably about 2 to about 12, more preferably about 3 to about 10 wt. % of one or more alkyl polyglucosides selected from lauryl glucoside, octyl glucoside, decyl glucoside, coco glucoside, and a mixture thereof, preferably lauryl glucoside, decyl glucoside, and a mixture thereof; and
      (iii-b) about 1 to about 20 wt. %, preferably about 2 to about 15, more preferably about 3 to about 12 wt. % of two or more of one or more fatty acid alkanolamides, wherein at least one of the fatty acid alkanolamides is an acyl glucamide and one of the fatty acid alkanolamides is not an acyl glucamide; and
(c) 40 to about 90 wt. %, preferably about 50 to about 85 wt. %, more preferably about 60 to about 80 wt. % of water; and
(d) optionally, about 0.01 to about 10 wt. %, preferably about 0.01 to about 5 wt. %, more preferably about 0.1 to about 5 wt. % of one or more amidoamines selected from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallowamidopropyl dimethylamine, brassicamidopropyl dimethylamine, olivamidopropyl dimethylamine, palmitamidopropyl dimethylamine, stearamidoethyldiethylamine, and a mixture thereof, preferably brassicamidopropyl dimethylamine;
   wherein all weight percentages are based on the total weight of the cleansing composition.

The surfactants of the surfactant system and the alkanolamides in the embodiment above may be any of those described throughout the instant disclosure. It is preferable that the one or more acyl glucamides are selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and a mixture thereof. Preferably, the composition includes lauroyl/myristoyl methyl glucamide. It is also preferably that the alkanolamides that are not acyl glucamides are selected from cocamide MEA and cocamide MIPA, cocamide DEA, cocamide DIPA, lauramide MEA, lauramide DEA, and a mixture thereof, preferably cocamide MIPA.

Additionally, as noted above, the anti-dandruff cleansing compositions do not require silicones, film-forming polymers, and sulfate-based surfactants. Thus, any one or more (or all) of these may optionally be excluded from the cleansing compositions. In other words, the compositions may be free or essentially free of silicones and/or film-forming polymers and/or sulfate-based surfactants. Nonetheless, in some instances, one or more silicones and/or one or more film-forming polymers and/or one or more sulfate-based surfactants may optionally be included in the cleansing compositions.

The viscosity of the cleansing compositions discussed throughout the instant disclosure (including all embodiments set forth above) can vary but is often similar to that of typical cleansing, shampooing, and/or conditioning compositions. Accordingly, in some instances, the viscosity can be from about 2500 cP to about 15,000 cp at a temperature of 25° C. The viscosity measurements can be carried out, for example, using a Brooksfield viscometer/rheometer using a RV-3 Disk spindle at a speed of 5, 10, 15, and/or 20 rpm or using a Rheomat with an M4 spindle. An RVDV-II+Pro Viscometer with RheocalcT software may be employed for automated instrument control and data acquisition. The test temperature is maintained at 25° C. by using a Brookfield TC-502P Programmable Refrigerated Bath. From its original container, a sample is transferred into a 600 mL beaker and then tested.

In some cases, the viscosity is from about 2000 cP to about 20,000 cP, about 2000 cP to about 15,000 cP, about 2000 cP to about 10,000 cP, about 2000 cP to about 8000 cP, about 2000 cP to about 6000 cP, about 3000 cP to about 20,000 cP, about 3000 cP to about 15,000 cP, about 3000 cP to about 10,000 cP, or about 3000 cP to about 8000 cP, about 3000 cP to about 6000 cP.

The cleansing compositions described throughout the instant disclosure may be in a variety of different forms, for example, gels, lotions, creams, milks, sprays, and the like. The cleansing compositions, however, are not typically in the form of an emulsion. Nonetheless, in some cases, the cleansing compositions may be in the form of a dispersion. Due to the cleansing and conditioning properties of the cleansing compositions, in some instances, the cleansing compositions may be designated as a "shampoo," a "conditioning shampoo," or an "all-in-one conditioning and shampooing composition." The cleansing compositions may also be a body wash or both a hair and body wash.

The anti-dandruff cleansing compositions described throughout the instant disclosure effectively deliver salicylic acid to the scalp for the treatment of dandruff. It is preferable that the anti-dandruff cleansing compositions are stable and maintain a homogenous texture (e.g., it is preferable that the components of the anti-dandruff cleansing compositions do not phase-separate). Thus, the instant disclosure relates to stable anti-dandruff cleansing compositions.

The term "stable" means that the compositions do not phase-separate for at least 8 weeks at a temperature of 4° C. Therefore, a "stable anti-dandruff cleansing compositions" refers to an anti-dandruff cleansing composition that does not visually phase-separate for at least 8 weeks at a temperature of 4° C. In fact, the stable anti-dandruff cleansing compositions typically do not visually phase separate for at least 8 weeks at even higher temperatures. For instance, the stable anti-dandruff cleansing compositions may not visually phase separate for at least 8 weeks at a temperature of 4° C., 25° C., 37° C., 45° C., and 60° C., as reported in Example 1, below. Accordingly, the instant disclosure relates to anti-dandruff cleansing compositions "that remain stable for at least 8 weeks at a temperature of 4° C., 25° C., 37° C., 45° C., and 60° C.," and relates to "anti-dandruff cleansing compositions" that remain stable for at least 8 weeks at a temperature range of 4° C. to 60° C." In other words, the instant disclosure relates to anti-dandruff cleansing compositions "that do not visually phase separate for at least 8 weeks at a temperature of 4° C., 25° C., 37° C., 45° C., and 60° C." and relates to "anti-dandruff cleansing compositions "that do not visually phase separate for at least 8 weeks at a temperature range of 4° C. to 60° C."

The anti-dandruff cleansing compositions of the instant disclosure are particularly useful for treating dandruff, and for cleansing and conditioning hair. Additionally, the anti-dandruff cleansing compositions provide a variety of desirable cosmetic and styling benefits to the hair, for example, smoothness, detangling, and shine. Accordingly, the cleansing compositions are useful in methods for treating dandruff, methods for cleansing hair, methods for conditioning hair, and methods for imparting smoothness, detangling, and/or shine to hair. Accordingly, the instant disclosure encompasses methods for treating hair with the anti-dandruff cleansing compositions of the instant disclosure. Such methods may include simply applying an anti-dandruff cleansing composition of the instant disclosure to the hair. The methods also include shampooing and/or conditioning the hair with an anti-dandruff cleansing composition of the instant disclosure. Such methods typically include applying an effective amount of an anti-dandruff cleansing composition of the instant disclosure to the hair, allowing the it to remain on the hair for a period of time, and subsequently rinsing it from the hair. The period of time for which the composition is allowed to remain on the hair is usually not long, e.g., not longer than about 5 minutes. Usually, the composition is merely allowed to remain on the hair for a period of time sufficient to incorporate the composition throughout the hair, for example, by lathering the composition throughout the hair using one's hands. The amount of time is sufficient for the composition to interact with the scalp, hair, and any dirt, oil, contamination, etc., that may exist on the scalp and hair so that when rinsed, the dirt, oil, contamination, etc., is effectively removed from the scalp and hair, and the conditioning agents of the cleansing composition can interact with the hair to provide conditioning benefits. Thus, the anti-dandruff cleansing composition may be allowed to remain on the hair for about 5 seconds to about 5 minutes, about 5 seconds to about 3 minutes, about 5 seconds to about 2 minutes, about 5 seconds to about 1 minute, about 30 seconds to about 5 minutes, or about 30 seconds to about 3 minutes.

As is common when using shampoo and/or conditioning compositions, the hair may be wetted or rinsed with water prior to application of an anti-dandruff cleansing composition of the instant disclosure. Having water already in the hair can be helpful for creating lather when applying the compositions because the water interacts with the surfactants of the surfactant system.

Implementation of the present disclosure is provided by way of the following examples. The examples serve to illustrate the technology without being limiting in nature.

Example 1

Anti-Dandruff Shampoo Compositions

| | | INCI US | A wt % | B wt % | C wt % | D wt % | E wt % | F wt % | G wt % |
|---|---|---|---|---|---|---|---|---|---|
| | Anti-Dandruff | SALICYLIC ACID | 2.9 | 3 | 3 | 3 | 3 | 3 | 3 |
| Anionic Surfactants | Isethionate | SODIUM ISETHIONATE | 0.2 | 0.2 | 0.2 | 0.2 | 0.2 | 0.2 | 0.2 |
| | | SODIUM COCOYL ISETHIONATE | 4.4 | 4.4 | 4.4 | 4.4 | 4.4 | 4.4 | 4.4 |
| Amphoteric Surfactants | Betaine | COCO-BETAINE AND/OR COCAMIDOPROPYL BETAINE | 7 | 7.2 | 7.2 | 3.6 | 7 | 7 | 7.2 |
| Nonionic Surfactants | Alkyl Polyglucoside(s) | LAURYL AND/OR DECYL GLUCOSIDE | 7 | 1.1 | 7.2 | 3.6 | 7 | 7 | 7.2 |
| | Amide Surfactant | LAUROYL/MYRISTOYL METHYL GLUCAMIDE | 7.6 | 7.8 | 7.8 | 7.8 | 7.6 | 7.6 | 3.9 |
| | | COCAMIDE MIPA | 2 | 2 | 2 | 2 | 1 | 1 | 2 |
| | Total Nonionic Surfactants | | 16.6 | 10.9 | 17 | 13.4 | 15.6 | 15.6 | 13.1 |
| Conditioning Agent | | BRASSICAMIDOPROPYL DIMETHYLAMINE | 0.5 | 0.5 | 0.5 | 0.5 | 0.5 | 0.5 | 0.5 |
| Water-Soluble Solvent | | GLYCERIN | 1 | 1 | 1 | 1 | 1 | 1 | 1 |
| Emollient | | HYDROGENATED COCONUT ACID | 0.4 | 0.4 | 0.4 | 0.4 | 0.4 | 0.4 | 0.4 |
| pH Adjuster | | SORBIC ACID, CITRIC ACID, SODIUM HYDROXIDE, Etc. | ≤2 | ≤2 | ≤2 | ≤2 | ≤2 | ≤2 | ≤2 |
| Salt | | SODIUM CHLORIDE | 1.5 | 1.3 | 1.3 | 0.7 | 1.3 | 1.5 | 1.3 |
| Extract | | VEGETAL EXTRACT | 0.2 | — | — | — | — | — | — |
| Water | | WATER | QS 100 | QS 100 | QS 100 | QS 100 | QS 100 | QS 100 | QS 100 |
| | | Stable | Y | Y | Y | Y | Y | Y | Y |

| | | INCI US | H wt % | I wt % | J wt % | K wt % | L wt % | M wt % |
|---|---|---|---|---|---|---|---|---|
| | Anti-Dandruff | SALICYLIC ACID | 3 | 3 | 3 | 3 | 3 | 3 |
| Anionic Surfactants | Isethionate | SODIUM ISETHIONATE | 0.2 | 0.2 | 0.2 | 0.2 | 0.2 | 0.2 |
| | | SODIUM COCOYL ISETHIONATE | 4.4 | 4.4 | 4.4 | 4.4 | 4.4 | 4.4 |

-continued

| | | | | | | | | |
|---|---|---|---|---|---|---|---|---|
| Amphoteric Surfactants | Betaine | COCO-BETAINE AND/OR COCAMIDOPROPYL BETAINE | 7.2 | 6.9 | 7.2 | 7.1 | 7.2 | 3.6 |
| Nonionic Surfactants | Alkyl Polyglucoside(s) | LAURYL AND/OR DECYL GLUCOSIDE | 3.6 | 7 | — | — | 1.1 | 1.1 |
| | Amide Surfactant | LAUROYL/MYRISTOYL METHYL GLUCAMIDE | 7.8 | 7.6 | 7.8 | 7.1 | 3.9 | 3.6 |
| | | COCAMIDE MIPA | 2 | 1 | 2 | 2 | 2 | 2 |
| | Total Nonionic Surfactants | | 13.4 | 15.6 | 9.8 | 15.6 | 7.0 | 6.7 |
| | Conditioning Agent | BRASSICAMIDOPROPYL DIMETHYLAMINE | 0.5 | 0.5 | 0.5 | 0.5 | 0.5 | 0.5 |
| | Water-Soluble Solvent | GLYCERIN | 1 | 1 | 1 | 1 | 1 | 1 |
| | Emollient | HYDROGENATED COCONUT ACID | 0.4 | 0.4 | 0.4 | 0.4 | 0.4 | 0.4 |
| | pH Adjuster | SORBIC ACID, CITRIC ACID, SODIUM HYDROXIDE, Etc. | ≤2 | ≤2 | ≤2 | ≤2 | ≤2 | ≤2 |
| | Salt | SODIUM CHLORIDE | 1.3 | 1.5 | 1.3 | — | 1.3 | 0.8 |
| | Extract | VEGETAL EXTRACT | — | — | — | — | — | — |
| | Water | WATER | QS 100 | QS 100 | QS 100 | QS 100 | QS 100 | QS 100 |
| | | Stable | Y | N | N | N | N | N |

Compositions A-M were prepared and subjected to stability testing. Samples from each of the compositions were stored for 8 weeks at temperatures of 4° C., 25° C., 37° C., 45° C., or 60° C. Each week the samples were visually evaluated for phase separation. The compositions that remained stable for the entire 8 week testing period at all temperatures are designated as stable in the table above with a "Y" (which represents "yes"). Compositions that phase separated before the end of the 8 week testing period at one or more of the various temperatures are designated as not stable in the table above with an "N" (which represents "no").

Compositions A-H, which include an alkyl polyglucoside and at least 10 wt. % of nonionic surfactants were stable. Compositions J and K, which did not include one or more alkyl polyglucosides, were not stable, notwithstanding the fact that Composition K included at least 10 wt. % of nonionic surfactants. Compositions L and M, which did not contain at least 10 wt. % of nonionic surfactants, were not stable, notwithstanding the fact that both of these compositions included one or more alkyl polyglucosides. This illustrates that both the alkyl polyglucosides and the high amount of nonionic surfactants have a stability influence on the compositions. Composition I was an anomaly because it was not stable even though it included one or more alkyl polyglucosides and contained more than 10 wt. % of nonionic surfactants. It is unclear why composition I is an outlier. The results of the testing illustrate that the plurality of nonionic surfactants in high amounts of at least 10 wt. % and the one or more alkyl polyglucosides surprisingly and unexpectedly provide stabilizing properties to the anti-dandruff cleansing compositions.

Example 2

Anti-Dandruff Action

Composition A of Example 1 was clinically tested on fourteen volunteers that suffer from dandruff, and its anti-dandruff effect compared with three commercial benchmark anti-dandruff shampoos. Commercial Benchmark 1 included 2% of salicylic acid as the anti-dandruff active. Commercial Benchmark 2 included 0.6% of selenium sulfide as the anti-dandruff active. Commercial Benchmark 3 included 1% pyrithione zinc as the anti-dandruff active. Several square inch areas of the scalp from both sides of the head of each volunteer were randomly selected and evaluated by experts for dandruff flakes. The experts determined the quantity of flakes per square inch before and after treatment with the various anti-dandruff shampoos. The experts found that treatment with Composition A of Example 1 resulted in less flakes compared to treatment with any of the three commercial benchmark shampoos. Thus, the experts concluded that treatment with Composition A of Example 1 was more effective at treating dandruff than any of the commercial benchmark shampoos.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The transitional phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−5% of the indicated number.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt. %, less than 0.1 wt. %, less than 0.05 wt. %, or less than 0.01 wt. %, or none of the specified material. Furthermore all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. An anti-dandruff shampoo composition consisting of:
   (a) 1 to 5 wt. % of salicylic acid;
   (b) 20 to 40 wt. % of a surfactant system consisting of:
      (i) about 2 to about 10 wt. % of one or more acyl isethionates, salts thereof, or a mixture thereof;
      (ii) about 2 to about 10 wt. % of one or more amphoteric surfactants; and
      (iii) at least 10 wt. % of one or more alkyl polyglucosides and one or more fatty acid alkanolamides,
         wherein at least one of the one or more fatty acid alkanolamides is a glucamide having a carbon chain length of 8 to 20,
         the one or more alkyl polyglucosides is in an amount of about 3 to about 10 wt. %,
         the one or more fatty acid alkanolamides is in an amount of about 3 to about 12 wt. %, and
         (b)(iii) is in an amount greater than a combined amount of (b)(i) and (b) (ii);
   (c) about 50 to about 80 wt. % of water;
   (d) about 0.01 to about 5 wt. % of one or more conditioning agents selected from the group consisting of alkylamines, cationic conditioning polymers, non-silicone fatty compounds, and a mixture thereof; and
   (e) about 0.1 to about 10 wt. % of one or more water-soluble solvents; and
   (f) optionally, one or more salts, preservatives, vegetal extracts, or pH adjusters;
      wherein the composition does not phase-separate for at least 8 weeks at a temperature of 4° C.; and
      all weight percentages are based on the total weight of the composition.

2. The composition of claim 1, wherein the one or more acyl isethionates, salts thereof, or a mixture thereof, are selected from the group consisting of sodium isethionate, sodium cocoyl isethionate, sodium lauroyl methyl isethionate, and sodium cocoyl methyl isethionate.

3. The composition of claim 1, wherein the one or more amphoteric surfactants are selected from the group consisting of betaines, alkyl amphoacetates, and alkyl amphopropionates.

4. The composition of claim 3, wherein at least one of the one or more amphoteric surfactants is a betaine.

5. The composition of claim 4 wherein the betaine is selected from the group consisting of coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, or mixtures thereof.

6. The composition of claim 1, wherein the one or more alkyl polyglucosides are selected from the group consisting of lauryl glucoside, octyl glucoside, decyl glucoside, and coco glucoside.

7. The composition of claim 1, wherein the one or more glucamides are selected from the group consisting of lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, cocoyl methyl glucamide, lauryl methylglucamide, oleoyl methylglucamide oleate, stearoyl methylglucamide stearate, and sunfloweroyl methylglucamide.

8. The composition of claim 1, wherein at least one of the one or more fatty acid alkanolamides is not a glucamide.

9. The composition of claim 8, wherein the at least one fatty acid alkanolamide that is not a glucamide is selected from the group consisting of cocamide MEA, cocamide MIPA, cocamide DEA, cocamide DIPA, lauramide MEA, and lauramide DEA.

10. The composition of claim 1, wherein at least one of the one or more conditioning agents is an alkylamine.

11. The composition of claim 1, wherein one or more water-soluble solvents are selected from the group consisting of glycerol and glycols.

12. A method for treating hair comprising contacting hair with the anti-dandruff shampoo composition of claim 1 and subsequently rinsing it from the hair.

13. A method for treating dandruff comprising contacting hair of an individual in need of treatment for dandruff with the anti-dandruff shampoo composition of claim 1 and subsequently rinsing it from the hair.

* * * * *